United States Patent [19]

Vale, Jr. et al.

[11] 4,393,050

[45] Jul. 12, 1983

[54] ANALOGS OF EXTENDED N-TERMINAL SOMATOSTATIN

[75] Inventors: Wylie W. Vale, Jr.; Jean E. F. Rivier, both of La Jolla; Marvin R. Brown, Del Mar, all of Calif.

[73] Assignee: The Salk Institute for Biological Studies, San Diego, Calif.

[21] Appl. No.: 258,878

[22] Filed: Apr. 29, 1981

[51] Int. Cl.$^3$ .................... A61K 37/00; C07C 103/52
[52] U.S. Cl. ............................ 424/177; 260/112.5 S
[58] Field of Search ................. 260/112.5 S; 424/177

[56] References Cited

U.S. PATENT DOCUMENTS 4,316,891 2/1982 Guillemin et al. ............ 260/112.5 S

FOREIGN PATENT DOCUMENTS 1551929 8/1976 United Kingdom .

OTHER PUBLICATIONS

FEBS Letters, Jan. 1980, vol. 109, No. 1, Biochem, and Biophys. Res. Comm., vol. No. 95, No. 3, pp. 945-951, 8/14/80 Ling et al. "Solid Phase Synthesis of Somatostatin-28.

Biochem. and Biophys. Res. Comm., vol. 96, No. 2, pp. 725-734, 9/30/80, Bohlen et al. "Isolation and Amino Acid Composition of Two Somatostatin-Like Peptides from Ovine Hypothalamus": Somatostatin-28 and Somatostatin-25.

*Primary Examiner*—Delbert R. Phillips
*Attorney, Agent, or Firm*—Fitch, Even, Tabin & Flannery

[57] ABSTRACT

Somatostatin-28 has the formula:

H-Ser-Ala-Asn-Ser-Asn-Pro-Ala-Met-Ala-Pro-Arg-Glu-Arg-Lys-

Ala-Gly-Cys-Lys-Asn-Phe-Phe-Trp-Lys-Thr-Phe-Thr-Ser-Cys-OH.

Analogs have been synthesized that are more potent than somatostatin-28, and these analogs or pharmaceutically acceptable salts thereof, dispersed in a pharmaceutically acceptable liquid or solid carrier, can be administered to mammals in the same manner as somatostatin. In the analogs, Leu may be substituted in the 8-position in combination with D-Trp in the 22-position and/or Tyr in the 25-position. D-Cys may also be substituted in the 28-position, and D-Ser may be substituted in the 27-position. Certain residues may also be deleted. D-Trp$^{22}$ somatostation-28 has surprisingly been found to be insulin-selective when administered in vivo and is useful for the treatment of insulinoma.

16 Claims, No Drawings

ANALOGS OF EXTENDED N-TERMINAL SOMATOSTATIN

The invention described herein was made in the course of work under a grant or award from the Department of Health and Human Services.

This invention is directed to peptides related to the tetradecapeptide somatostatin and to methods for pharmaceutical treatment of mammals using such peptides. More specifically, the invention relates to analogs of somatostatin-28, to pharmaceutical compositions containing such analogs and to methods of treatment of mammals using such analogs.

BACKGROUND OF THE INVENTION

The tetradecapeptide somatostatin was characterized by Guillemin et al. and is described in U.S. Pat. No. 3,904,594 (Sept. 9, 1975). The tetradecapeptide has the formula:

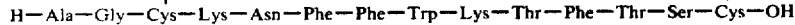
H—Ala—Gly—Cys—Lys—Asn—Phe—Phe—Trp—Lys—Thr—Phe—Thr—Ser—Cys—OH wherein there is a bridging bond between the sulfhydryl groups of the two cysteinyl amino acid residues. The tetradecapeptide in its linear form (sometimes referred to as dihydrosomatostatin), wherein this bridging bond is not present and is replaced by hydrogen, is for purposes of this application considered to be included in the definition "somatostatin" as it appears to have substantially the same biological activity.

Somatostatin and many analogs of somatostatin exhibit activity in respect to the inhibition of growth hormone (GH) secretion from cultured, dispersed rat anterior pituitary cells in vitro and also in vivo and with respect to the inhibition of insulin and glucagon secretion in vivo in the rat and in other mammals. Somatostatin has also been found to inhibit the secretion of gastrin and secretin by acting directly upon the secretory elements of the stomach and pancreas respectively. The powerful inhibitory effects of somatostatin on the secretion not only of GH but also of insulin and glucagon have led to studies of a possible role of somatostatin in the management or treatment of juvenile diabetes and have proved useful in studying the physiological and pathological effects of these hormones on human metabolism. In juvenile-type diabetics, somatostatin diminishes fasting hyperglycemia by as much as 50 percent in the complete absence of circulating insulin.

In view of its ability to inhibit the secretion of such hormones, somatostatin may be therapeutically employed in clinical conditions for the treatment of acromegaly, pancreatic islet cell tumors and diabetes mellitus. Because somatostatin has a relatively short duration of action, apparently because it is inactivated by peptidases when administered in vivo, the search has continued for longer-acting somatostatin materials, as well as for somatostatin analogs which are more potent than somatostatin or which are both more potent and exhibit dissociated inhibitory functions.

L. Pradayrol, et al. in *FEBS Letters* 109, Jan. 1980, pp 55-58, reported the isolation and characterization of somatostatin-28 (SS-28) from porcine upper small intestine. Testings of synthetic SS-28 showed increased potency when administered in vivo, and further iprovements were sought.

SUMMARY OF THE INVENTION

Analogs of the 28-residue peptide somatostatin-28 have been prepared and purified (i.e. substantially free of related synthetic replicates) which, when tested in vitro and in vivo, are more potent than somatostatin-28 in inhibiting the release of GH, glucagon and insulin. The 28-member peptide is hereinafter referred to as SS-28 and has the formula:

H-Ser-Ala-Asn-Ser-Asn-Pro-Ala-Met-Ala-Pro-Arg-Glu-Arg-Lys-

Ala-Gly-Cys-Lys-Asn-Phe-Phe-Trp-Lys-Thr-Phe-Thr-Ser-Cys-OH

The analogs may include the following substitutions: Leu for Met in the 8-position; D-Trp for Trp in the 22-position; Tyr for Phe in the 25-position; D-Ser for Ser in the 27-position and D-Cys for Cys in the 28-position. Certain residues may also be deleted.

Pharmaceutical compositions in accordance with the invention include SS-28 analogs, or nontoxic addition salts thereof, dispersed in a pharmaceutically acceptable liquid or solid carrier. The administration of such somatostatin-28 analogs or pharmaceutically acceptable addition salts thereof to mammals in accordance with the invention may be carried out for the regulation of secretion of growth hormone, insulin and/or glucagon. Analogs having D-Trp in the 22-position are insulin-selective and may be used for the treatment of insulinoma.

DETAILED DESCRIPTION OF THE PREFERRED EMBODIMENTS

Somatostatin-28 has been earlier isolated from porcine intestinal extract and has recently been isolated from ovine hypothalamic extracts. The nomenclature used to define the peptides is that specified by Schroder & Lubke, "The Peptides", Academic Press (1965) wherein, in accordance with conventional representation, the amino group appears to the left and the carboxyl group to the right. Where the amino acid residue has isomeric forms, it is the L-form of the amino acid that is represented unless otherwise expressly indicated.

The invention provides analogs of SS-28 having the following formula:

H—Ser—Ala—Asn—Ser—Asn—Pro—Ala—R$_8$—Ala—Pro—Arg—Glu—Arg—Lys—Ala

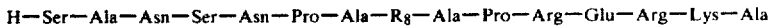
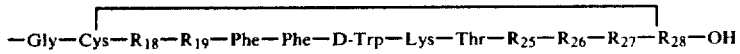
—Gly—Cys—R$_{18}$—R$_{19}$—Phe—Phe—D-Trp—Lys—Thr—R$_{25}$—R$_{26}$—R$_{27}$—R$_{28}$—OH wherein R$_8$ is Met or Leu, R$_{18}$ is Lys or des R$_{18}$, R$_{19}$ is Asn or des R$_{19}$, R$_{25}$ is Phe or Tyr, R$_{26}$ is Thr or des R$_{26}$, R$_{27}$ is Ser or D-Ser and R$_{28}$ is D-Cys or Cys, with at least one R-group being deleted or different from SS-28. Although not specifically shown herein, the formula should be understood also to include the linear form thereof wherein the bridge between the sulfhydryl groups of Cys residues is not present and is replaced by hydrogen.

The peptides are synthesized by a suitable method, such as by exclusively solid-phase techniques, by partial solid-phase techniques, by fragment condensation or by classical solution addition. For example, the techniques of exclusively solid-state synthesis are set forth in the textbook "Solid-Phase Peptide Synthesis", Stewart & Young, Freeman & Co., San Francisco, 1969 and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues linked to the side-action protecting groups.

Also considered to be within the scope of the present invention are intermediates of the formula:

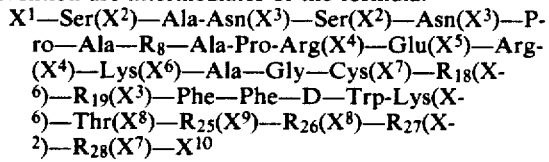

$X^1$—Ser($X^2$)—Ala-Asn($X^3$)—Ser($X^2$)—Asn($X^3$)—Pro—Ala—$R_8$—Ala-Pro-Arg($X^4$)—Glu($X^5$)—Arg-($X^4$)—Lys($X^6$)—Ala—Gly—Cys($X^7$)—$R_{18}$($X^6$)—$R_{19}$($X^3$)—Phe—Phe—D—Trp-Lys($X^6$)—Thr($X^8$)—$R_{25}$($X^9$)—$R_{26}$($X^8$)—$R_{27}$($X^2$)—$R_{28}$($X^7$)—$X^{10}$ wherein: the R-groups are as hereinbefore defined; $X^1$ is either hydrogen or an α-amino protecting group. The α-amino protecting groups contemplated by $X^1$ are those known to be useful in the art in the step-wise synthesis of polypeptides. Among the classes of α-amino protecting groups covered by $X^1$ are (1) acyl-type protecting groups, such as formyl, trifluoroacetyl, phthalyl, p-toluenesulfonyl(Tos), benzensulfonyl, nitrophenylsulfenyl, tritylsulfenyl, o-nitrophenoxyacetyl, chloroacetyl, acetyl, and γ-chlorobutyryl; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl(trityl), benzyl(Bzl); (7) trialkylsilane groups, such as trimethylsilane. The preferred α-amino protecting group is BOC.

$X^2$ and $X^8$ are protecting groups for the hydroxyl group of Thr and Ser and are preferably selected from the class consisting of acetyl(Ac), benzoyl(Bz), tert-butyl, trityl, tetrahydropyranyl, benzyl ether(Bzl), 2,6-dichlorobenzyl and Z. The most preferred protecting group is Bzl. $X^2$ and/or $X^8$ can be hydrogen, which means there is no protecting group on the hydroxyl group.

$X^3$ is hydrogen or a protecting group for the amido group of Asn and is preferably xanthyl(Xan).

$X^4$ is a protecting group for the guanidino group of Arg preferably selected from the class consisting of nitro, Tos, Z, adamantyloxycarbonyl and BOC, or is hydrogen. Tos is most preferred.

$X^5$ is hydrogen or an ester-forming protecting group for the γ-carboxyl group of Glu preferably selected from the class consisting of Bzl, 2,6-dichlorobenzyl(DCB), CBZ, methyl and ethyl. OBzl is most preferred.

$X^6$ is hydrogen or a protecting group of the side chain amino substituent of Lys. Illustrative of suitable side chain amino protecting groups are Z, 2-chlorobenzyloxycarbonyl(2-Cl-Z), Tos, t-amyloxycarbonyl and BOC. The selection of a side chain amino protecting group is not critical except that it must be one which is not removed during deprotection of the α-amino groups during the synthesis. Hence, the α-amino protecting group and the side chain amino protecting group cannot be the same.

$X^7$ is a protecting group for Cys preferably selected from the class consisting of p-methoxybenzyl(MeOBzl), p-methylbenzyl, acetamidomethyl, trityl and Bzl. The most preferred protecting group is p-methoxybenzyl. $X^6$ can also be hydrogen, meaning that there is no protecting group on the sulfur.

$X^9$ is a protecting group for the hydroxyl group of Tyr preferably selected from the class consisting of 2,6-dichlorobenzyl(DCB), Bzl, MeOBzl and OBzl. The most preferred is DCB.

$X^{10}$ is selected from the class consisting of OH, $OCH_3$, amides, hydrazides and esters, including a benzyl ester or a hydroxymethyl ester anchoring bond used in solid phase synthesis for linking to a solid resin support, represented by the formulae:

—O—$CH_2$-polystyrene resin support and

O—$CH_2$-benzyl-polystyrene resin support

The polystyrene polymer is preferably a copolymer of styrene with about 0.5 to 2% divinyl benzene as a crosslinking agent, which causes the polystyrene polymer to be completely insoluble in certain organic solvents.

In the formula for the intermediate, at least one of $X^1$, $X^2$, $X^3$, $X^4$, $X^5$, $X^6$, $X^7$, $X^8$ and $X^9$ is a protecting group. In selecting a particular side chain protecting group to be used in the synthesis of the peptides, the following rules are followed: (a) the protecting group must be stable to the reagent and under the reaction conditions selected for removing the α-amino protecting group at each step of the synthesis, (b) the protecting group must retain its protecting properties and not be split off under coupling conditions and (c) the side chain protecting group must be removable, upon the completion of the synthesis containing the desired amino acid sequence, under reaction conditions that will not alter the peptide chain.

The peptides are preferably prepared using solid phase synthesis, such as that described by Merrifield, J. Am. Chem. Soc., 85, p 2149 (1964), although other equivalent chemical syntheses known in the art can also be used as previously mentioned. Solid-phase synthesis is commenced from the C-terminal end of the peptide by coupling a protected α-amino acid to a suitable resin. Such a starting material can be prepared by attaching α-amino- and S-protected Cys to a chloromethylated resin or to a hydroxymethyl resin. The preparation of the hydroxymethyl resin is described by Bodansky et al., Chem. Ind. (London) 38, 1597-98 (1966). Chloromethylated resins are commercially available from Bio Rad Laboratories, Richmond, California and from Lab. Systems, Inc. The preparation of such a resin is described by Stewart et al., "Solid Phase Peptide Synthesis" (Freeman & Co., San Francisco 1969), Chapter 1, pp 1-6.

Cys protected by BOC and by p-methoxybenzyl is coupled to the chloromethylated polystyrene resin according to the procedure of Monahan and Gilon, Biopolymer 12, pp 2513-19, 1973. Following the coupling of BOC-(p-methoxybenzyl)(Cys) to the resin support, the α-amino protecting group is removed, as by using trifluoroacetic acid(TFA) in methylene chloride, TFA alone or with HCl in dioxane. Preferably 50 weight % TFA in methylene chloride is used with 0-5 weight %, 1,2 ethane-dithiol. The deprotection is carried out at a temperature between about 0° C. and room temperature. Other standard cleaving reagents and conditions for removal of specific α-amino protecting groups may be used as described in Schroder & Lubke, "The Peptides", 1 pp 72-75 (Academic Press 1965).

After removal of the α-amino protecting group of Cys, the remaining α-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are: (1) carbodiimides, such as N,N'-diisopropyl carbodiimide, N-ethyl-N'-(3-dimethylaminopropyl)carbodiimide; (2) cyanamides such as N,N'-dibenzylcyanamide; (3) ketei-mines; (4) isoxazolium salts, such as N-ethyl-5-phenyl isoxazolium-3'-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N'-carbonyl diimidazole, N,N'-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) nitrogen-containing heterocyclic compounds having a hydroxy group on one ring nitrogen, such as N-hydroxyphthalimide, N-hydroxysuccinimide and 1-hydroxybenzotriazole(HOBT). Other activating reagents and their use in peptide coupling are described by Schroder & Lubke, supra, in Chapter III and by Kapoor, J. Phar. Sci., 59, pp 1-27 (1970).

Each protected amino acid or amino acid sequence is introduced into the solid phase reactor in about a four-fold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., Anal. Biochem. 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., Biopolymers, 1978, 17, pp. 1927-1938.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$, $X^7$, $X^8$ and $X^9$ and the α-amino protecting group $X^1$, to obtain the peptide in its linear form. The cyclic form of the peptide is obtained by oxidizing using a ferricyanide solution, preferably as described Rivier et al., Biopolymers, Vol. 17 (1978), 1927-38, or by air oxidation, or in accordance with other known procedures.

As an alternative route, the intermediate peptide may be separated from the resin support by alcoholysis after which the recovered C-terminal ester is converted to the acid by hydrolysis. Any side chain protecting groups may then be cleaved as previously described or by other known procedures, such as catalytic reduction (e.g. Pd on $BaSO_4$) using conditions which will keep the Trp moiety intact. When using hydrogen fluoride for cleaving, anisole and methylethyl sulfide are included in the reaction vessel for scavenging. When Met is present in the sequence, the BOC protecting group is cleared with trifluoroacetic acid(TFA)/ethane-dithiol prior to cleaving from the resin to eliminate S-alkylation; and furthermore, cleavage from the resin is carried out in the presence of methyl ethyl sulfide as a scavenger.

The following Example sets forth the preferred method for synthesizing analogs of SS-28 by the solid-phase technique.

EXAMPLE 1

The synthesis of the analog [$Leu^8$, $D$-$Trp^{22}$, $Tyr^{25}$]-SS-28 having the formula:

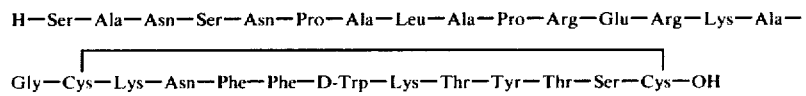

is conducted in a stepwise manner on a chloromethylated resin, such as LS-601 available from Lab Systems, Inc., containing 0.9 Meq Cl/gm. resin. Coupling of BOC-(p-methoxybenzyl)Cys to resin is performed by the procedure set forth by Horiki et al., in *Chemistry Letters* (Chem. Soc. of Japan) (1978) pp. 165-168, and it results in the substitution of about 0.35 mmol. Cys per gram of resin. All solvents that are used are carefully degassed, preferably by sparging with an inert gas, e.g. helium, to insure the absence of oxygen that might undesirably oxidize the sulfur of the Met residue or the Trp.

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC-Trp or BOC-Arg(Tos) or BOC-Asn(Xan) is being coupled, a mixture of 10% DMF and methylene chloride is used. Bzl is used as the hydroxyl side-chain protecting group for Ser and Thr. P-nitrophenyl ester-(ONp) is used to activate the carboxyl end of Asn, and BOC-Asn(ONp) is coupled overnight using one equivalent of HOBt in a 50% mixture of DMF and methylene chloride. 2—Cl—Z is used as the protecting group for the Lys side chain and DCB is used to protect Tyr. Tos is used to protect the guanidino group of Arg, and the glutamic carboxyl group is protected by OBzl. The amido group of Asn is protected by Xan. At the end of the synthesis, the following composition is obtained BOC—Ser(Bzl)—Ala—Asn(Xan)—Ser(Bz-
l)—Asn(Xan)—Pro—Ala—Leu—Ala—Pro-
—Arg(Tos)—Glu(OBzl)—Arg(Tos)—Lys(2—
Cl—Z)—Ala—Gly—Cys(MeOBzl)—Lys(2—
Cl—Z)—Asn(Xan)—Phe—Phe—D—Trp—Lys(-
2—Cl—Z)—Thr(Bzl)—Tyr(DCB)—Thr(Bz-
l)—Ser(Bzl)—Cys(MeOBzl)—O—$CH_2$-ben-
zenepolystyrene resin support.

In order to cleave and deprotect the resulting protected peptide-resin, it is treated with 1.5 ml. anisole, and 15 ml. hydrogen fluoride (HF) per gram of peptide-resin, first at −20° C. for 20 min. and then at 0° C. for one-half hour. After elimination of the HF under high vacuum, the resin-peptide is washed alternately with dry diethyl ether and chloroform, and the peptides are then extracted with de-gassed 2 N aqueous acetic acid and separated from the resin by filtration.

The cleaved and deprotected peptide is then added dropwise to a potassium ferricyanide solution to form the disulfide bond between the Cys residues, as described by Rivier et al. in *Biopolymers*, Volume 17 (1978) pp. 1927–1938. After cyclization, the peptide is chromatographed on both anion- and cation-exchange resins using the methods described in the Rivier et al. article and then lyophilized.

The peptide is then purified by gel permeation followed by semi-preparative HPLC as described in Rivier et al., *Peptides: Structure and Biological Function* (1979) pp. 125–128. The chromatographic fractions were carefully monitored by HPLC, and only the fractions showing substantial purity were pooled.

Specific optical rotation of the SS-28 analog, which was synthesized and purified in the foregoing manner, was measured on a Perkin Elmer Model 141 as $[\alpha]_D^{22°} = -77.5° \pm 0.5$ c = 1 in 1% acetic acid) and had a purity of about 96%. To check whether the precise sequence was achieved, the SS-28 analog was hydrolyzed in sealed evacuated tubes containing 4 N methanesulfonic acid and 0.2% tryptamine for 24 hours at 110° C. Amino acid analyses of the hydrolysates using a Beckman 121 MB amino acid analyzer showed that the 28-residue peptide structure had been obtained. The other SS-28 analogs listed in Table I were also synthesized and purified using the same method as set forth above.

TABLE I

| Peptide | Composition | Purity | $[\alpha]_D^{22°}$ |
|---|---|---|---|
| 1 | [Leu$^8$, D-Trp$^{22}$, Tyr$^{25}$]—SS-28 | 96 | −77.5° |
| 2 | [D-Trp$^{22}$, D-Cys$^{28}$]—SS-28 | 97 | |
| 3 | desAsn$^{19}$[D-Trp$^{22}$, D-Ser$^{27}$]—SS-28 | 96 | |
| 4 | desAA$^{18,19,26}$[D-Trp$^{22}$,D-Cys$^{28}$]—SS-28 | >98 | −87.7° |
| 5 | [D-Trp$^{22}$]—SS-28 | >98 | |
| 6 | [Leu$^8$, D-Trp$^{22}$]—SS-28 | >98 | |

EXAMPLE II

To determine the effectiveness of the peptides to inhibit the release of growth hormone, in vitro radioimmunoassays are carried out using the SS-28 analogs in side-by-side comparison with equimolar concentrations of somotostatin-14 having a known effectiveness to inhibit the release of growth hormone induced by the application of isobutyl methyl xanthine to pituitary cells. Cultures are used which include cells of rat pituitary glands removed some four to five days previously in a system that minimizes enzymatic degradation, generally following the procedure set forth in Vale et al., *Methods in Enzymology, Hormones and Cyclic Nucleotides* (1975) Vol. 37, p. 82. Both cultures of a defined standard medium and cultures which are considered optimal for the secretion of growth hormone, as a result of having additions of either 2% or 10% of serum from a foetal calf, are used for the comparative testing. The results of this comparative testing are set forth in Table II.

In vivo experiments are carried out with the SS-28 analogs, using the procedure described in Brown et al., *Metabolism* (1976) Vol. 25, pp. 1501–1503, to determine the potency, relative to somatostatin-14 to inhibit the secretion of glucagon and insulin stimulated by the administration of arginine to groups of six rats.

TABLE II

| Peptide | In Vitro Growth Hormone | In Vivo Glugacon | In Vivo Insulin |
|---|---|---|---|
| SS-14 | 1 | 1 | 1 |
| 1 | 4.84 | | |
| 2 | 3 | | |
| 3 | 0.1 | 1 | 145 |
| 4 | 1.51 | 14 | 18 |
| 5 | 2.93 | 27 | 2612 |
| 6 | | | |

The SS-28 analogs tested exhibit surprisingly increased potency and are considered to inhibit basal and stimulated insulin and glucagon secretion in mammals, including humans and dogs. These peptides are believed to have a direct effect upon the pancreatic cells to inhibit insulin and glucagon release. Accordingly, the administration to mammals of an effective amount of the SS-28 analogs (or a non-toxic, pharmaceutically acceptable addition salt thereof) can be used to inhibit the release of insulin and glucagon in mammals and may be employed in the treatment of diabetes in the same general manner as somatostatin is presently being administered. Likewise, administration of these peptides to mammals in effective amounts can inhibit the release of growth hormone and can be used for this purpose, under the guidance of a physician, and for the treatment of acromegaly in accordance with clinical procedures heretofore developed using somatostatin-14 and analogs thereof. These SS-28 analogs when administered intracisternally or into the lateral ventricle of rats or dogs inhibit the release of epinephrine from the adrenal gland and lower blood pressure. Under some circumstances, they decrease gastric acid secretion and influence thermoregulation.

It was very surprising to discover that [D-Trp$^{22}$]-SS-28 exhibited such an extreme insulin-selectivity, as can be seen from the comparison with SS-14 in the terms of which Table II reports the test results. As a result, this peptide is found to be particularly valuable for the treatment of insulinoma which would otherwise result in the secretion of large quantities of insulin and resultant hypoglycemia.

SS-28 analogs or  e nontoxic addition salts thereof, combined with a ph  naceutically acceptable carrier to form a pharmaceut  l composition, may be administered to mammal.,  luding humans, either intravenously, subcutaneously, intramuscularly, intranasally or orally. The administration may be employed by a physician to inhibit the release of growth hormone where the host being treated requires therapeutic treatment for excess secretion of somatotropin, which is associated with conditions such as juvenile diabetes and acromegaly. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, pamoate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptide should be administered under the guidance of a physician, and pharmaceutical compositions will usually contain the peptide in conjunction with a conventional, pharmaceutically-acceptable carrier. Usually, the dosage will be from about 2 to about 200 micrograms of the peptide per kilogram of the body weight of the host. Overall, treatment of subjects with these peptides is generally carried out in the same manner as the treatment using somatostatin itself.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the somatostatin peptide chain can be made in accordance with present or future developments without detracting from the potency of the analogs, and such peptides are considered as being within the scope of the invention. As earlier indicated, the linear form as well as the preferred cyclic form of the SS-28 analogs is considered to be within the scope of the invention.

Various features of the invention are emphasized in the claims which follow.

What is claimed is:

1. A pharmaceutical composition for decreasing gastric acid secretion comprising an effective amount of an analog of SS-28 having the formula:

H-Ser-Ala-Asn-Ser-Asn-Pro-Ala-Leu-Ala-Pro-Arg-Glu-Arg-

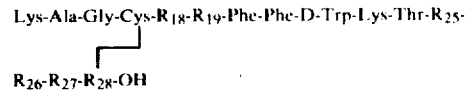

wherein $R_{18}$ is Lys or des $R_{18}$, $R_{19}$ is Asn or des $R_{19}$, $R_{25}$ is Phe or Tyr, $R_{26}$ is Thr or des $R_{26}$, $R_{27}$ is Ser or D—Ser and $R_{28}$ is D—Cys or Cys, or a nontoxic addition salt thereof, and a pharmaceutically acceptable liquid or solid carrier therefor.

2. The composition of claim 1 wherein $R_{18}$ is Lys, $R_{19}$ is Asn, $R_{26}$ is Thr, $R_{27}$ is Ser and $R_{28}$ is Cys.

3. The composition of claim 2 wherein $R_{25}$ is Phe.

4. The composition of claim 2 wherein $R_{25}$ is Tyr.

5. A method of inhibiting the release of growth hormone, insulin, adrenal epenephrine and or glucagon in a mammal or modifying the temperature regulation or the gastrointestinal function of a mammal, which method comprises administering to said mammal an effective amount of a material selected from the class consisting of analogs of SS-28 having the formula:

H-Ser-Ala-Asn-Ser-Asn-Pro-Ala-Leu-Ala-Pro-Arg-Glu-Arg-

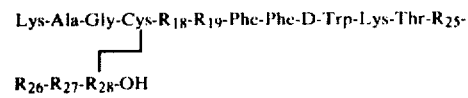

wherein $R_{18}$ is Lys or des $R_{18}$, $R_{19}$ is Asn or des $R_{19}$, $R_{25}$ is Phe or Tyr, $R_{26}$ is Thr or des $R_{26}$, $R_{27}$ is Ser or D-Ser and $R_{28}$ is D-Cys or Cys and the nontoxic acid addition salts thereof.

6. A method in accordance with claim 5 wherein said administering is carried out either orally, intravenously, subcutaneously, intranasally or intramuscularly.

7. The method of claim 5 wherein $R_{18}$ is Lys, $R_{19}$ is Asn, $R_{26}$ is Thr, $R_{27}$ is Ser and $R_{28}$ is Cys.

8. The method of claim 5 wherein $R_{25}$ is Phe.

9. The method of claim 5 wherein $R_{25}$ is Tyr.

10.

H-Ser-Ala-Asn-Ser-Asn-Pro-Ala-Leu-Ala-Pro-Arg-Glu-Arg-

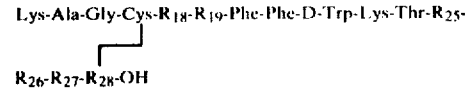

wherein $R_{18}$ is Lys or des $R_{18}$, $R_{19}$ is Asn or des $R_{19}$, $R_{25}$ is Phe or Tyr, $R_{26}$ is Thr or des $R_{26}$, $R_{27}$ is Ser or D-Ser and $R_{28}$ is D—Cys or Cys, or the linear version thereof where the disulfide bridge is replaced by hydrogen.

11. The compound of claim 10 wherein $R_{18}$ is Lys, $R_{19}$ is Asn, $R_{26}$ is Thr, $R_{27}$ is Ser and $R_{28}$ is Cys.

12. The compound of claim 11 wherein $R_{25}$ is Phe.

13. The compound of claim 11 wherein $R_{25}$ is Tyr.

14.

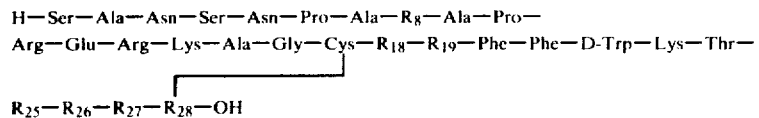

wherein $R_8$ is Met or Leu, $R_{18}$ is Lys or des $R_{18}$, $R_{19}$ is Asn or des $R_{19}$, $R_{25}$ is Phe or Tyr, $R_{26}$ is Thr or des $R_{26}$, $R_{27}$ is Ser or D-Ser and $R_{28}$ is D-Cys or Cys, provided however that when $R_{27}$ is Ser, $R_{28}$ is D-Cys, or the linear version thereof where the disulfide bridge is replaced by hydrogen.

15. The compound of claim 14 wherein $R_8$ is Met, $R_{18}$ is Lys, $R_{25}$ is Phe, $R_{27}$ is D-Ser and $R_{28}$ is Cys.

16. The compound of claim 14 wherein $R_8$ is Met, $R_{18}$ is des $R_{18}$, $R_{26}$ is des $R_{26}$, $R_{25}$ is Phe, $R_{27}$ is Ser and $R_{28}$ is D-Cys.

* * * * *